US010203290B2

(12) United States Patent
Ferro et al.

(10) Patent No.: US 10,203,290 B2
(45) Date of Patent: Feb. 12, 2019

(54) METHOD FOR DEFECT INDICATION DETECTION

(71) Applicant: General Electric Company, Schenectady, NY (US)

(72) Inventors: Andrew Frank Ferro, West Chester, OH (US); Xingwei Yang, Schenectady, NY (US); Paulo Ricardo dos Santos Mendonca, Clifton Park, NY (US); Christopher Allen Nafis, Rexford, NY (US); Patrick Joseph Howard, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 291 days.

(21) Appl. No.: 15/100,567

(22) PCT Filed: Dec. 1, 2014

(86) PCT No.: PCT/US2014/067895
§ 371 (c)(1),
(2) Date: May 31, 2016

(87) PCT Pub. No.: WO2015/088803
PCT Pub. Date: Jun. 18, 2015

(65) Prior Publication Data
US 2016/0305895 A1    Oct. 20, 2016

Related U.S. Application Data

(60) Provisional application No. 61/915,239, filed on Dec. 12, 2013.

(51) Int. Cl.
*G21K 1/02* (2006.01)
*G01N 23/18* (2018.01)
(Continued)

(52) U.S. Cl.
CPC .......... *G01N 23/18* (2013.01); *A61B 6/5282* (2013.01); *A61B 6/586* (2013.01); *G01N 23/046* (2013.01)

(58) Field of Classification Search
CPC ............. G01B 23/18; G01N 2223/401; G01N 2223/051; A61B 6/466; A61B 6/4085; A61B 6/482; A61B 6/032
See application file for complete search history.

(56) References Cited

U.S. PATENT DOCUMENTS 4,891,829 A    1/1990 Deckman et al.
6,163,589 A    12/2000 Vartanian
(Continued)

FOREIGN PATENT DOCUMENTS

CN    1449722 A    10/2003
CN    1565001 A    1/2005
(Continued)

OTHER PUBLICATIONS

Hopkins et al: "Analytical Corrections for Beam-Hardening and Object Scatte in Volumetric Computed Tomography Systems", 16th World Conference of Nondestructive Testing, Sep. 1, 2004.
(Continued)

*Primary Examiner* — Don Wong
(74) *Attorney, Agent, or Firm* — General Electric Company; William Andes

(57) ABSTRACT

Methods, apparatus and computer-readable media for detecting potential defects in a part are disclosed. A potential defect may be automatically detected in a part, and may be reported to an operator in various ways so that the operator may review the defect and take appropriate action.

12 Claims, 7 Drawing Sheets

(51) Int. Cl.
*A61B 6/00* (2006.01)
*G01N 23/046* (2018.01)

(56) References Cited

U.S. PATENT DOCUMENTS

| | | | |
|---|---|---|---|
| 2006/0093082 A1 | 5/2006 | Numata et al. | |
| 2009/0279772 A1 | 11/2009 | Sun | |
| 2010/0140485 A1 | 6/2010 | Mishra | |
| 2010/0278440 A1 | 11/2010 | Dragovich | |
| 2013/0165788 A1 | 6/2013 | Osumi et al. | |
| 2018/0266970 A1* | 9/2018 | Suppes | G01N 23/046 |

FOREIGN PATENT DOCUMENTS

| | | |
|---|---|---|
| CN | 1584568 A | 2/2005 |
| CN | 1853570 A | 11/2006 |
| CN | 101095165 A | 12/2007 |
| CN | 101688917 A | 3/2010 |
| CN | 102901773 A | 1/2013 |
| CN | 103169496 A | 6/2013 |
| DE | 102013104720 A1 | 11/2013 |
| EP | 0905509 A1 | 3/1993 |
| JP | S63-067551 A | 3/1988 |
| JP | S63-243852 A | 10/1988 |
| JP | S63-308548 A | 12/1988 |
| JP | H08-140964 A | 6/1996 |
| JP | H11-296700 A | 10/1999 |
| JP | 2004-062777 A | 2/2004 |
| JP | 2005-056087 A | 3/2005 |
| JP | 2006-125960 A | 5/2006 |
| JP | 2006-266754 A | 10/2006 |
| JP | 2006-329917 A | 12/2006 |
| JP | 2008-104761 A | 5/2008 |
| JP | 2008-104762 A | 5/2008 |
| JP | 2009-034478 A | 2/2009 |
| JP | 2010-038878 A | 2/2010 |
| JP | 2010-057572 A | 3/2010 |
| JP | 2010-201089 A | 9/2010 |
| JP | 2013-150778 A | 8/2013 |

OTHER PUBLICATIONS

Huang et al: "Visualizing Industrial CT Volume Data for Nondestructive Testing Applications", Annual IEEE Conference on Visualization, Jan. 1, 2003.

Seitel et al: "Adaptive Bilateral Filter for Image Denoising and Its Application to In-Vitro Time-Of-Flight Data", Medical Imaging 2001: Visualization, Image-Guided Procedures, and Modeling, Spie, Mar. 3, 2011.

PCT Search Report issued in connection with corresponding Application No. PCT/US2014/067895 dated Mar. 4, 2015.

First Office Action and Search issued in connection with corresponding CN Application No. 201480067761.7 dated May 10, 2018.

Japanese Search Report issued in connection with corresponding JP Application No. 2016-538055 dated Apr. 26, 2017.

Notification of Reasons for Refusal issued in connection with corresponding JP Application No. 2016-538055 dated May 9, 2017.

* cited by examiner

METHOD FOR DEFECT INDICATION DETECTION

CROSS-REFERENCE TO RELATED APPLICATIONS

This PCT utility application claims priority to and benefit from currently pending provisional application having U.S. Patent Application Ser. No. 61/915,239, titled "Method for Defect Indication Detection" and having filing date Dec. 12, 2013, all of which is incorporated by reference herein.

BACKGROUND

The disclosed embodiments generally pertain to one or more methods of detecting defect indications in parts, as well as to apparatus configured to implement selected aspects of the disclosed methods, and computer-readable media (transitory and non-transitory) configured to cause a computing system to perform selected aspects of the disclosed methods. More particularly, but not by way of limitation, present embodiments relate to automatic detection of defect indications in a part using volumetric computed tomography (VCT)-based data. As used herein, a "defect indication" or "indication" may refer to a portion or area of a volume that potentially may have a defect. The term "indication" will be primarily used herein.

Industrial inspection increasingly is being performed using three-dimensional (3D) volumes. A VCT scan may be performed, e.g., on a composite aircraft part under inspection, to generate a 3D stack, or "volume," of 2D images, or "slices," of the part. A human operator then may individually review each 2D slide to identify indication of defects typically found in composite parts, such as porosity issues and delamination.

Slice-by-slice 2D inspection of a 3D model can be time consuming, laborious and/or error prone. The operator may be required to review a large number of 2D slices of the 3D volume, alone and in relation to each other, in order to determine whether there are defects in the entire volume. For example, the operator may be required to observe subtle changes in grayscale occurring over multiple 2D images. This process is time consuming, tedious and error prone. It is also likely that the analysis will vary greatly across operators, as well as between stages of an operator's shift, e.g., due to operator fatigue.

Previous attempts to automate aspects of defect indication detection have had various problems. For instance, to reduce beam hardening and scattering artifacts, pixels or voxels of a 3D volume of a part have been "normalized" to a "standard," e.g., an aluminum rod. However, adding a rod to the field of view may degrade the images, and this approach only works with linear computed tomography (CT) scans, not VCT. Moreover, this approach requires little or no geometric variance between the shape of the part and the shape of the standard.

In view of the aforementioned challenges and issues, it would be desirable to automate as many steps of the defect detection process as possible, so that the operator is less likely to make mistakes, will be able to review more parts per shift, and so that part inspection will be more consistent across operators and shifts.

SUMMARY

According to one aspect, a VCT-based method for notifying a user of a potential defect in a composite part may include obtaining VCT scan data representing a 3D volume of the composite part, normalizing the 3D volume against a generated background of the composite part that includes beam hardening and/or scattering artifacts, detecting an indication of the potential defect in the normalized 3D volume, and outputting information about the indication to the user.

According to another aspect, a VCT-based method for notifying a user of a potential defect in a composite part may include: importing data from a VCT acquisition apparatus over one or more computer networks, the data representing a plurality of associated parts; segmenting a subset of data from the imported data, the subset representing an individual part of the plurality of associated parts; performing assisted defect recognition to identify and classify indications of potential defects in the subset; and reporting the indications of identified and classified potential defects to an operator.

In various embodiments, apparatus may be configured to perform selected aspects of the above-described methods. In various embodiments, computer-readable media (transitory and non-transitory) may include instructions configured to cause one or more computing devices to perform selected aspects of the above-described methods.

All of the above outlined features are to be understood as exemplary only and many more features and objectives of the method may be gleaned from the disclosure herein. Therefore, no limiting interpretation of this summary is to be understood without further reading of the entire specification, claims, and drawings included herewith.

BRIEF DESCRIPTION OF THE ILLUSTRATIONS

Embodiments are illustrated in the following illustrations wherein.

Figure 8:
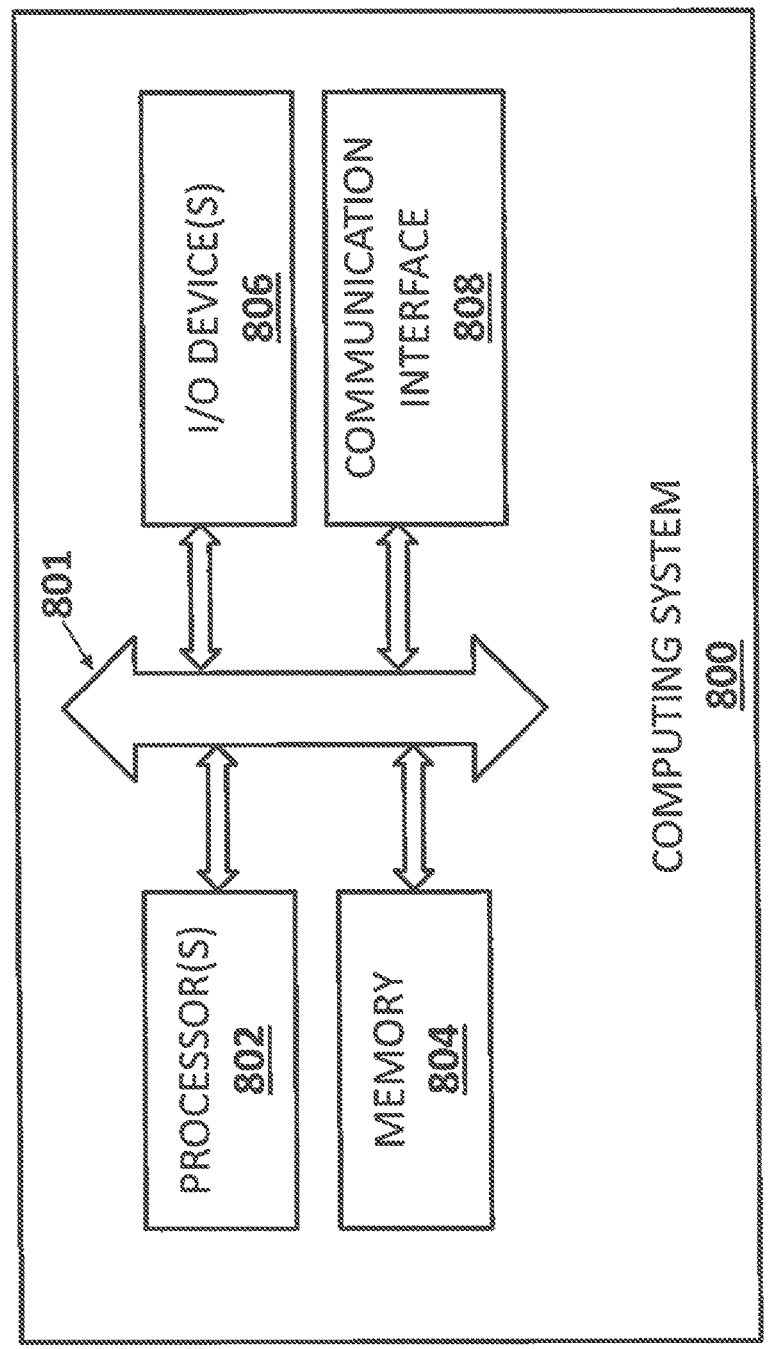

FIG. 8 schematically depicts example components of a computing device that may be configured to perform selected aspects of various methods described herein, in accordance with various embodiments.

DETAILED DESCRIPTION

Reference now will be made in detail to embodiments provided, one or more examples of which are illustrated in the drawings. Each example is provided by way of explanation, not limitation of the disclosed embodiments. In fact, it will be apparent to those skilled in the art that various modifications and variations can be made in the present embodiments without departing from the scope or spirit of the disclosure. For instance, features illustrated or described as part of one embodiment can be used with another embodiment to still yield further embodiments. Thus it is intended that the present invention covers such modifications and variations as come within the scope of the appended claims and their equivalents.

Figure 1:
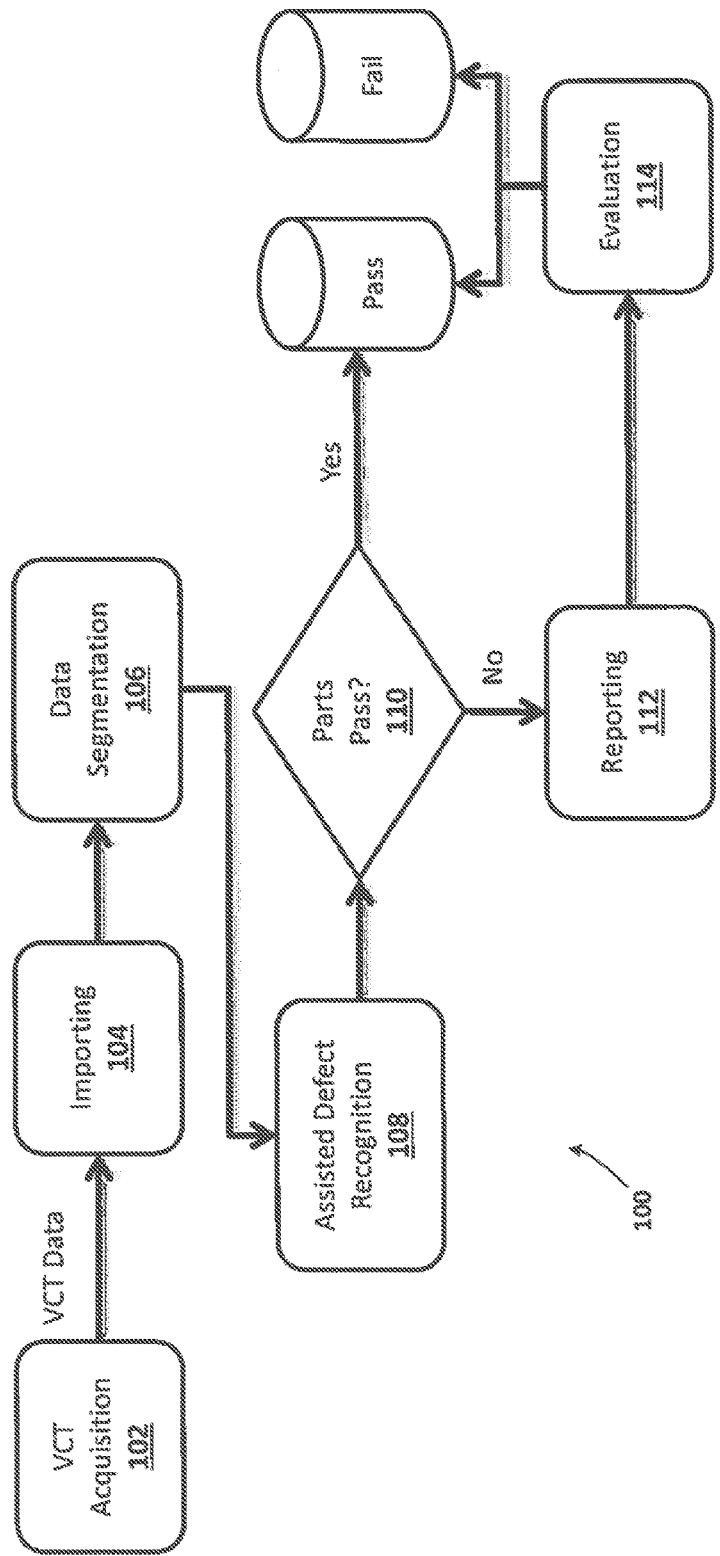
FIG. 1 is a flow chart showing operations of a VCT-based method for notifying an operator of an indication of a potential defect in a part, in accordance with various embodiments.

FIG. 1 schematically depicts, at a relatively high level, an example VCT-based method 100 for notifying a user of an indication of a potential defect in a part. Various aspects of method 100 will be depicted and described herein in more detail below. At block 102, VCT data may be obtained, e.g., by feeding one or more parts through a VCT scanning system. At block 104, the VCT data may be imported into a database or other memory accessible by a computing system (e.g., 800 of FIG. 8) configured with selected aspects of the present disclosure. At block 106, the imported data may be segmented, e.g., by part. For example, data associated with a 3D volume may be segregated or otherwise distinguished from data representing volumes of other parts. In some embodiments, a connected volume may be selected, extracted, and autocropped.

At block 108, assisted defect recognition (ADR) may be performed. As will be described in more detail below, in various embodiments, ADR may include normalizing voxels of a 3D volume to itself, denoising the volume using various techniques, and using techniques such as region growing to detect and/or classify indications of potential defects. At block 110, it may be determined based on the analysis performed at block 108 whether the part under examination satisfies a predetermined criterion. If the answer is yes (e.g., the part shows no indications of potential defects), then an indication that the part passed may be stored, e.g., in a "pass" database.

If the answer at block 110 is no, on the other hand, then at block 112, various information may be reported to an operator so that the operator may then review the potential detect more closely to determine whether the part truly fails, or whether the automatically perceived indication is minor enough that the part should pass. For instance, in some embodiments, the computing system may render, e.g., on a display, a 3D representation of the part with the detected indication superimposed over it or otherwise rendered on the representation. Additionally or alternatively, in some embodiments, the operator may be provided with data related to the indication, such as a signal strength associated with the indication. In various embodiments, "signal strength" may refer to any measurement of how probable the indication is to being rejectable. Various measurements may be used, such as a percentage drop (e.g., from neighboring voxels), a signal to noise ratio, a contrast to noise ratio, amplitude, and so forth.

At block 114, based on data provided to the operator at block 112, the operator may determine whether the part should pass (e.g., the indication is not of a critical nature) or if it should fail. The operator may provide his or her input to the computing system, which may then store an indication of whether the part passed or failed. By having operations 108-112 performed automatically by one or more computing systems, the operator may be spared from having to review every 2D slice of the 3D volume, alone and in relation to neighboring slices, to determine whether there are indications of potential defects in the part.

Figure 2:
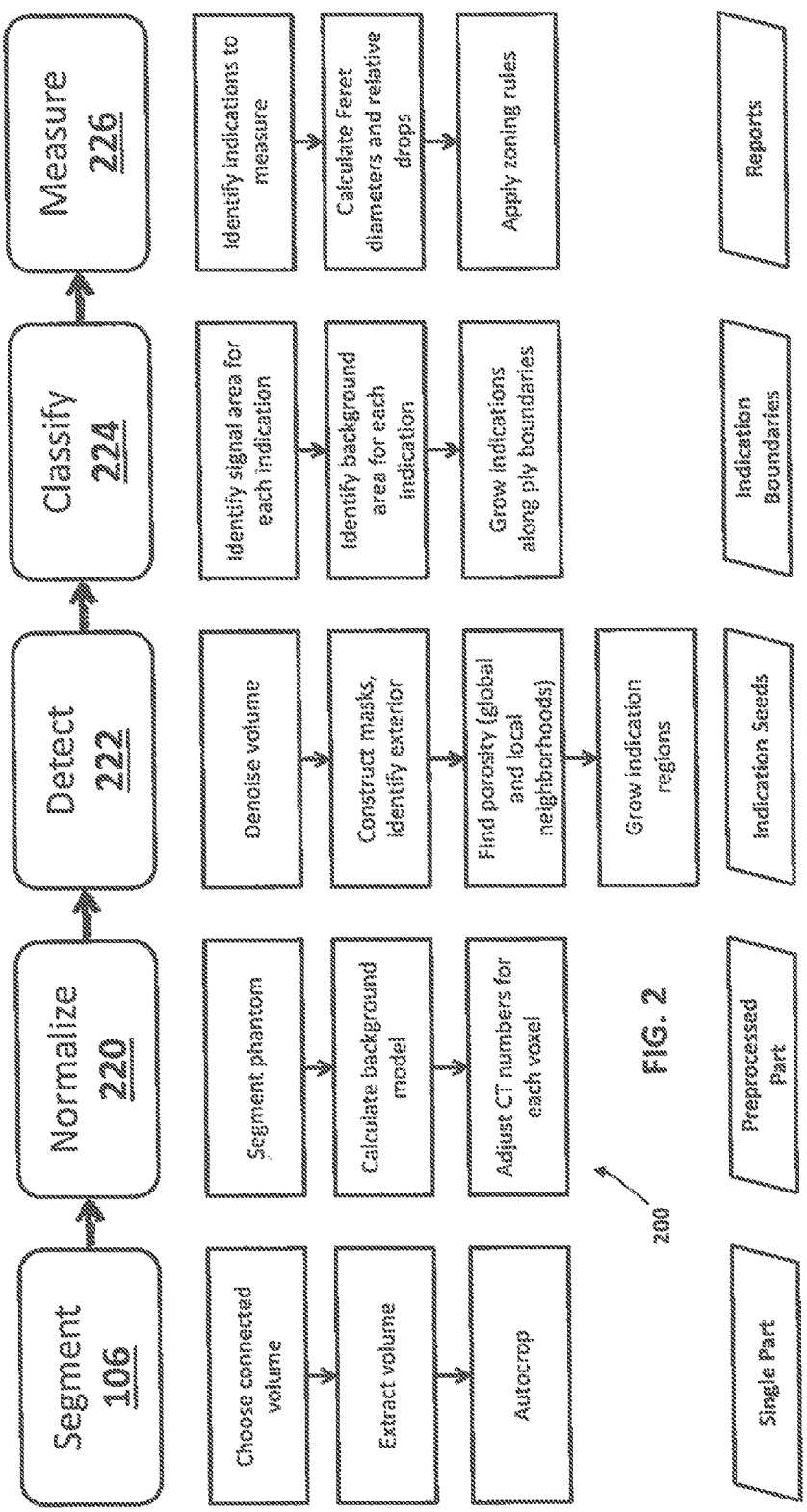
FIG. 2 is another flow chart showing operations of an embodiment of a VCT-based method for notifying an operator of an indication of a potential defect in a part, in accordance with various embodiments.

FIG. 2 is a lower level schematic depiction of a method 200 that may be implemented as part of method 100 of FIG. 1. Block 106 (segmentation) is depicted again to demonstrate where in method 100 the operations of FIG. 2 may (but are not required to) occur. As shown below block 106 in FIG. 2, the segmentation may include choosing a connected volume (e.g., from a plurality of connected volumes), extracting that volume, and autocropping that volume so that portions of other connected volumes are eliminated. In various embodiments, output of operations associated with block 106 may include a 3D volume of a single part for inspection.

At block 220, the autocropped volume may be normalized to reduce and/or eliminate artifacts introduced by phenomenon like beam hardening and scattering. In various embodiments, the volume may be normalized to itself. For instance, in various embodiments, a 3D "background" volume of the part may be generated. The background model may be smoothed, e.g., using a non-local means filter, so that beam hardening and/or scattering artifacts, as well as edges, are preserved. Voxels of a 3D volume of the part may then be normalized, voxel by voxel, against the background volume. For example, in some embodiments, the background volume may be subtracted from the 3D volume of the part, effectively removing beam hardening and scattering artifacts. The operations performed in association with block 220 may also be referred to as "artifact removal." In some embodiments, output of the various operations associated with block 220 may be a preprocessed part.

Figure 3:
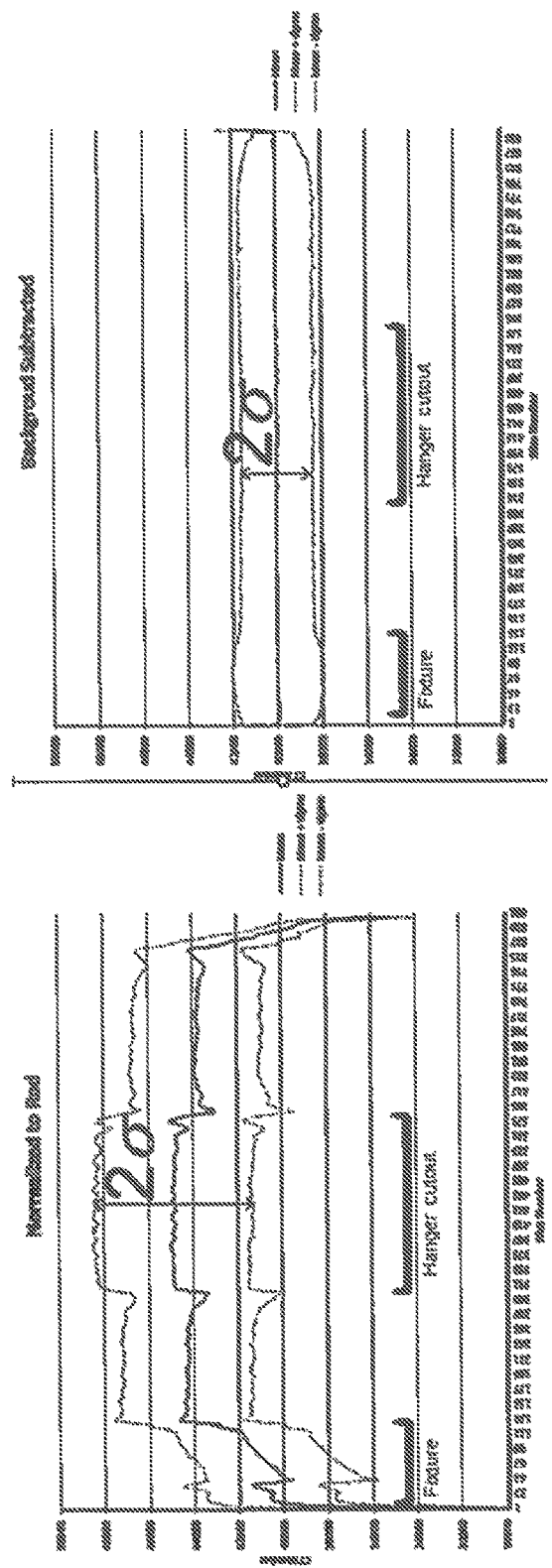
FIG. 3 depicts example results obtained through various normalization techniques, in accordance with various embodiments.

FIG. 3 depicts example results 300 from normalizing VCT scans of a part with a hanger cutout that was fixtured in the VCT scanner. The fixture and the cutout may adversely affect normalization—it is expected that a slice should be constant through the part because the part is of uniform density. On the left, the VCT scans were normalized against a standard aluminum rod. On the right, the VCT scans were normalized by subtracting a background volume, as described in association with FIG. 2. It can be seen that sigma times two ($2\sigma$) is far greater on the left than it is on the right.

Referring back to FIG. 2, at block 222, one or more indications of potential defects may be detected in the normalized volume. In some embodiments, the normalized volume may first be "de-noised." VCT numbers, e.g., CT scan numbers, may vary with a maximum CT path length. This may be especially true with complex geometries. To avoid noise from longer path lengths infecting lower path length sections, and to avoid false positive rates in different areas of a part, the 3D volume of the part may be de-noised, slice by slice, based on a priori knowledge of variance versus CT path length.

In some embodiments, a bilateral filter, which may or may not be adaptive, may be employed, e.g., to preserve edges. A distance map may be calculated to approximate maximum path length in a given slice of the 3D VCT volume. Smoothing power may be determined by a similarity value, a range value (e.g., minimum edge strength), $\sigma_r$, and a spatial extent, $\sigma_s$. In some embodiments, a linear regression model may be empirically fit to the similarity value and the maximum path length. In some embodiments, the following equation may be used:

$$\sigma_r = m \times d_{max} + b$$

Where m and b are regression parameters for a linear model, and $d_{max}$ is the maximum path length in a slice.

Operations associated with the detect block 222 may also include construction of masks used to identify an exterior (e.g., an edge) of the part. A porosity of the part may be determined, e.g., globally in the part and in local neighborhoods. In some embodiments, operations associated with block 222 may be used to identify "seeds," or seed voxels, which may indicate where in the 3D volume indications of potential defects may exist. In some embodiments, indications may be shaded in various hues, colors, brightness levels, etc., to distinguish them from adjacent areas.

In various embodiments, regions of the 3D volume where indications of potential defects are detected may be "grown," e.g., to encompass the entirety of an indication of a potential defect. Starting with the seed voxel, a region growing algorithm may be executed to "grow" a region around the seed by sequentially evaluating neighboring voxels based on various criteria. If neighboring voxels satisfy the criteria, they may be added, thereby growing the region of the indication of the potential defect. Region growing operations associated with the detect block 222 may be "best effort" operations.

At block 224, indications may be classified. In some embodiments, classification may include classifying a potential defect indication as significant enough to be presented to the operator. In some embodiments, classification may include analyzing pixels/voxels that were shaded during operations associated with block 222. Various classification decisions may be made about those shaded pixels/voxels. In some embodiments, it may be determined whether a group of shaded pixels/voxels actually indicates multiple separate defects. In some embodiments, it may be determined whether two separate groups of shaded pixels/voxels are actually indicative of a single large defect. In some embodiments, potential defect indications may be grown in a direction normal to a plane defined by a slice of the 3D volume. These techniques may reduce or eliminate false positives. In some embodiments, a signal area for each indication of a potential defect may be identified. A background area for each indication of a potential defect may also be identified.

In some embodiments, indications of potential defects may be grown once again using region grown algorithms. This time, however, the indications may be grown along boundaries defined in a computer-aided design (CAD) model of the part. Composite parts such as ceramic matrix composites may be built in layers. In many instances, indications of potential defects in such parts do not extend across layers. This characteristic of composite parts may be leveraged to guide and/or assist in growing regions. Voxels on the same ply as a seed voxel may be much more likely to satisfy the region growing criterion than voxels on a neighboring ply.

Figure 4:
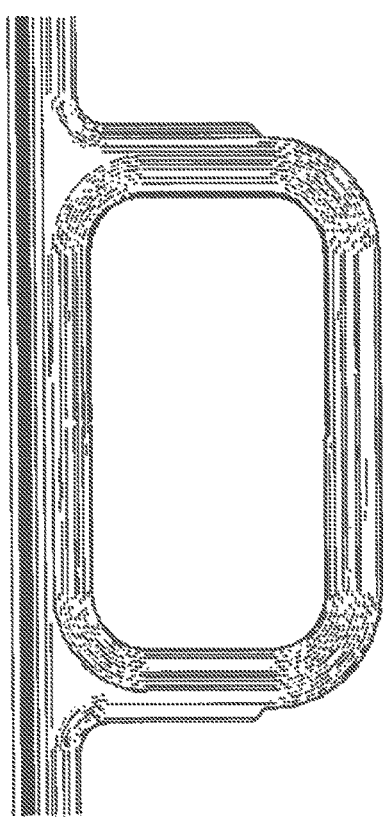
FIG. 4 depicts a ply model of a composite part, in accordance with various embodiments.
Figure 5:
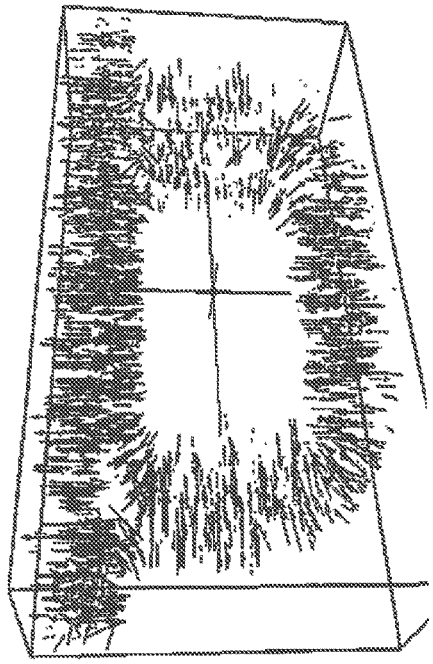
FIG. 5 depicts an example vector field that may be generated based on the ply model of FIG. 4, in accordance with various embodiments.

FIG. 4 depicts an example of a ply model image 400 of a part 402. FIG. 5 depicts a vector field 500 that may be generated from the stacked ply model of FIG. 4. In various embodiments, each voxel $v_i$ to be evaluated may be associated with a vector $F_i$ in the vector field that demonstrates a direction in which indications of potential defects are less likely to grow into (e.g., towards an adjacent layer). For each voxel $v_i$ to be evaluated, a growing direction $G_i$ from $v_i$ to a source voxel $v_j$ may be calculated by $G_i = v_i - v_j$. In various embodiments, a user may provide two pairs of thresholds for evaluating whether a given voxel $v_i$ should be added to a growing region. One pair may be a coarse criterion (e.g., $coarse_{min}$ and $coarse_{max}$) that is orthogonal to the growing direction $G_i$. The other pair may be a stricter, fine criterion (e.g., $fine_{min}$ and $fine_{max}$) that is parallel to the growing direction $G_i$. In each case, the minimum may be selected to be less than a current pixel/voxel and the maximum may be selected to be greater than the current pixel/voxel. In some embodiments, a combined criterion C may be determined by the following formula:

$$C = (1-\alpha) \times C_1 + \alpha \times C_2$$

where $\alpha$ is the inner product between growing direction $G_i$ and vector direction $F_i$, $C_1$ is the loose pair of thresholds and $C_2$ is the stricter pair of thresholds. C may be the dynamically generated thresholds for the voxel under evaluation.

In various embodiments, one region growing process that begins at one seed voxel associated with one indication of a potential defect may not interact or interfere with another region growing process that starts with another seed voxel associated with another indication. Accordingly, in various embodiments, region growing processes for each seed voxel may each be executed in its own thread of a multi-threaded environment. In some embodiments, the output of operations associated with block 224 may include indication boundaries.

Referring back to FIG. 2, at block 226, the indications of potential defects within the indication boundaries output by the operations associated with block 224 may be measured, e.g., to provide the operator with sufficient data to determine how to address an indication of a potential defect. Feret diameters may be determined for each indication. A signal strength may be calculated as well, e.g., based on the background of each indication identified in the operations associated with block 224. A percentage drop (or another signal strength measurement) from neighboring CT pixel/voxel values may be determined.

In some embodiments, "zoning rules" may also be applied to determine whether indications are worthy of being flagged for operator review. Zoning rules may include different rejection criteria for different regions (i.e. "zones") of the part. For example, an indication detected in a first region of the part may not be likely to cause trouble downstream, e.g., because defects in that region may not be likely to impact downstream performance. However, an indication detected in a second region (e.g., a very thin or fragile portion of the part, or a zone of high internal residual stress) may be more likely to cause downstream performance issues, such as failure of the part. Thus, different criteria may be used for the first and second regions, respectively, to determine whether to notify the operator of those indications.

In various embodiments, the output of operations associated with block 226 may be one or more reports to the operator in various forms. In some embodiments, the 3D volume of the part may be rendered on a display device. Any indications that satisfied the zoning rules described above may be superimposed or otherwise rendered on the 3D volume. Additionally or alternatively, raw data about each indication—e.g., its signal strength, percent drop off from neighboring voxels, etc.—may be reported to the operator, e.g., in a spread sheet. The operator may then use this output data to make a determination about each indication (e.g., is it significant enough to reject the part?).

Figure 6:
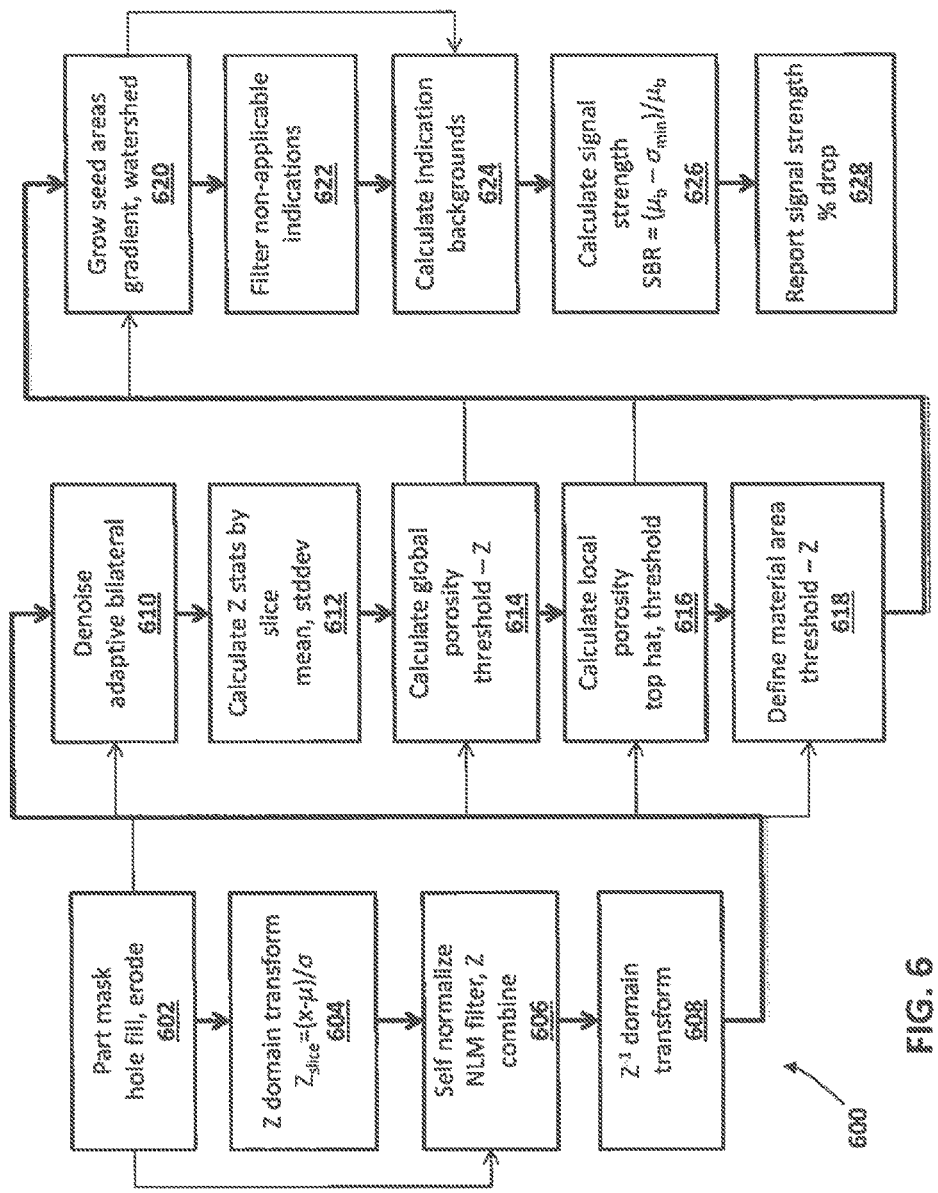
FIGS. 6 and 7 depict more flow charts showing operations of two more embodiments of methods for notifying an operator of an indication of a potential defect in a part, in accordance with various embodiments.

FIG. 6 depicts, in more detail than FIG. 1 or 2, an example process 600 for detecting indications and flagging them for an operator. At block 602, a part mask may be generated, and hole fill and erode image processing operations may be performed. At block 604, a Z domain transform may be performed, e.g., to transform the 3D model and the generated background to the Z-domain (e.g., by mean and standard deviation) so that they can be combined accurately. In some embodiments, this transformation may be performed using an equation such as the following:

$$Z_{slice} = (x - \mu)/\sigma$$

where x represents one thing, $\mu$ represents a mean of a slice, and $\sigma$ represents a standard deviation of the slice.

At block 606, the 3D volume of the part may be self-normalized as described above with relation to the operations associated with block 220 of FIG. 2, e.g., using a non-local means ("NLM" in FIG. 6) filter. As described above, in some embodiments, a Z-combine operation may also be performed using the 3D volume and a calculated background volume. For example, both the 3D volume of the part and the generated background may be subtracted in the Z-domain. At block 608, an inverse Z transformation ($Z^{-1}$) may be performed on the 3D volume.

At block 610, the denoising described above in association with block 222 of FIG. 2 may be performed, e.g., using the aforementioned adaptive bilateral filter. At block 612, Z statistics such as mean and standard deviation may be calculated per slice.

At block 614, a global porosity may be calculated. For instance, in some embodiments, a global threshold calculation may be performed on the preprocessed volumes. At block 616, a local porosity may be calculated, e.g., by calculating a top hat transform and then comparing the result to a threshold. At block 618, a material area—i.e. an area of an image in which it is likely that few or no defects will be found—may be defined.

At block 620, seed regions (e.g., starting at seed voxels) may be grown as described above. In some embodiments, gradient and/or watershed image processing techniques may be employed to grow regions. At block 622, indications of potential defects that do not satisfy various criteria may be filtered out. At block 624, backgrounds for the remaining indications of potential defects may be calculated. At block 626, a signal strength (e.g., percentage drop, or "SBR") for each indication of a potential defect may be calculated, e.g., using equations such as the following:

$$SBR = (\mu_b - \sigma_{min})/\mu_b$$

where $\mu_b$ represents a mean and $\sigma_{min}$ represents a standard deviation. At block 628, a percentage drop in signal strength may be reported, e.g., to the operator, so that the operator can decide what further action should be taken.

Figure 7:
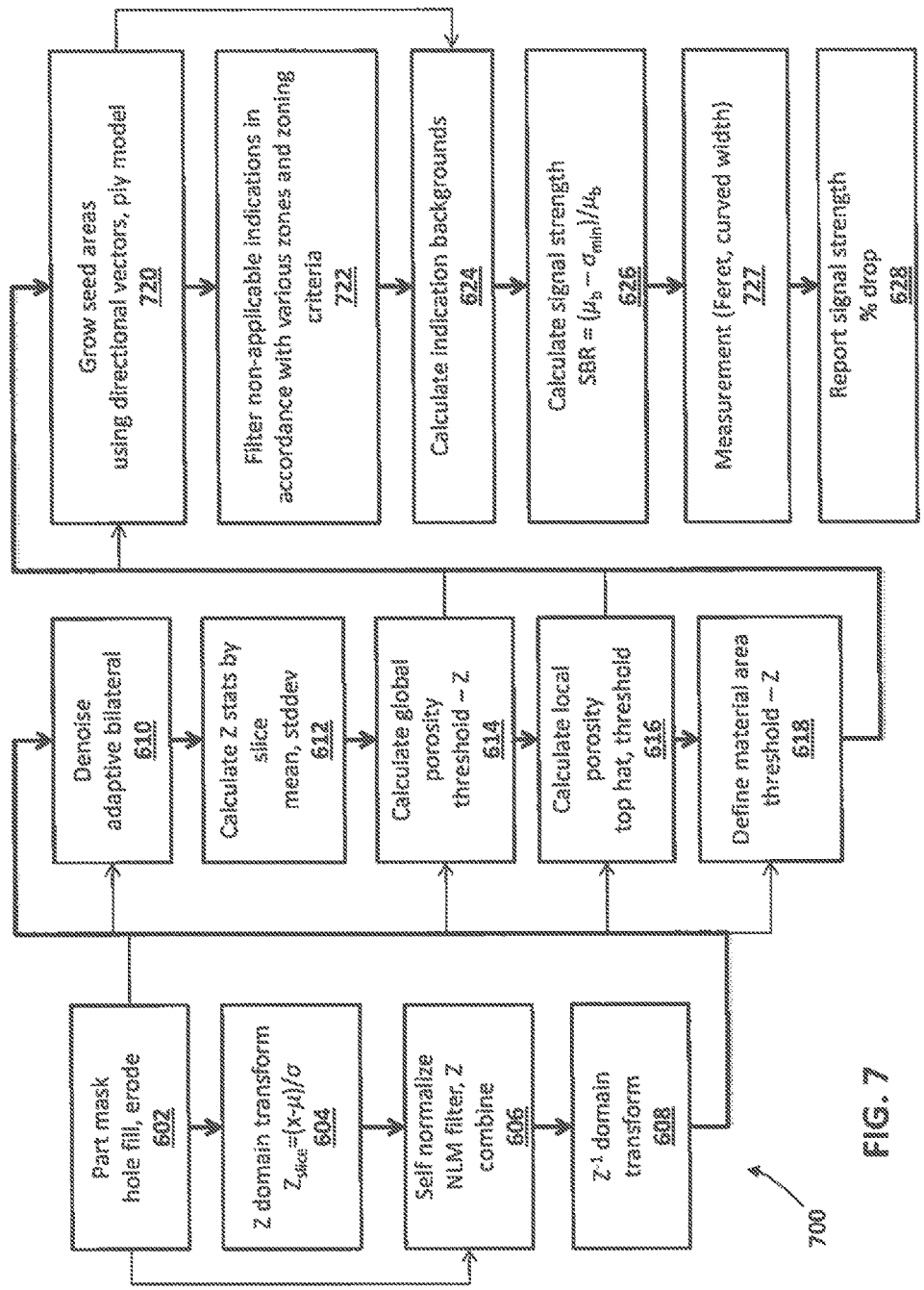

FIG. 7 depicts a method 700 that is very similar to method 600 of FIG. 6, and thus most blocks are labeled identically. However, block 620 of method 600 is replaced with block 720, in which directional vectors are used in conjunction with a ply composite model as described above in order to grow regions. Additionally, block 622 is replaced with block 722, in which non-applicable indications are filtered in accordance with various zones of the part, as well as with zoning criteria associated with each zone, as described above. Finally, new operation 727 is added in which various measurements (e.g., Feret diameter, curved width) of each indication may be calculated.

FIG. 8 depicts an example computing system 800 that may be configured to implement various aspects of the selected disclosure, including but not limited to selected aspects of methods 100, 200, 600 and 700. Computing system 800 may include one or more buses 801 that may be used to operably couple various computing components. The various computing components may include, but are not limited to, one or more processors 802, memory 804 (RAM, ROM, HD, etc.), one or more input/output devices 806 (e.g., keyboard, mouse, display, printer, etc.), one or more communication interfaces 808 (e.g., wired or wireless), and so forth. In various embodiments, computing system 800 may receive VCT scanned data from a VCT scanning system (not shown), e.g., via communication interface 808, and may perform selected aspects of the present disclosure to flag indications in a part for operator review.

The foregoing description of structures and methods has been presented for purposes of illustration. It is not intended to be exhaustive or to limit the structures and methods to the precise forms and/or steps disclosed, and obviously many modifications and variations are possible in light of the above teaching. Features described herein may be combined in any combination. Steps of a method described herein may be performed in any sequence that is physically possible. It is understood that while certain forms of composite structures have been illustrated and described, it is not limited thereto and instead will only be limited by the claims, appended hereto.

While multiple inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Examples are used to disclose the embodiments, including the best mode, and also to enable any person skilled in the art to practice the apparatus and/or method, including making and using any devices or systems and performing any incorporated methods. These examples are not intended to be exhaustive or to limit the disclosure to the precise steps and/or forms disclosed, and many modifications and variations are possible in light of the above teaching. Features described herein may be combined in any combination. Steps of a method described herein may be performed in any sequence that is physically possible.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. A volumetric computed tomography (VCT)-based method for providing notification of a potential defect in a composite part, comprising:
   obtaining (102) VCT scan data representing a three-dimensional (3D) volume of the composite part;
   normalizing (220) the 3D volume against a generated background of the composite part that includes beam hardening and/or scattering artifacts;
   detecting (222) an indication of the potential defect in the normalized 3D volume; and
   outputting (112) information about the indication.

2. The VCT-based method of claim 1, wherein the outputting comprises rendering, on a display (806), a 3D image of the composite part that includes the indication.

3. The VCT-based method of claim 1, further comprising determining (224) a boundary of the detected indication based at least in part on a computer-aided design (CAD) model, wherein the information about the indication includes information about the boundary.

4. The VCT-based method of claim 3, further comprising:
   identifying (222) a seed voxel of the indication; and
   performing (620, 720) region growing around the seed voxel.

5. The VCT-based method of claim 4, wherein the CAD model is a ply model (400) of the composite part, and growth of the region around the seed voxel is constrained by the ply model.

6. The VCT-based method of claim 1, further comprising denoising (610) the normalized 3D volume using an adaptive bilateral filter.

7. The VCT-based method of claim 1, further comprising denoising (606) the normalized 3D volume using a non-local means filter.

8. The VCT-based method of claim 1, further comprising:
   identifying (224) a signal area of the indication; and
   identifying (220) a background of the indication based on a computer-aided design (CAD) model.

9. The VCT-based method of claim 8, further comprising calculating (226) a signal strength of the indication based on the signal area and the background of the indication.

10. The VCT-based method of claim 9, wherein the normalizing includes generating (602) a part mask of the composite part.

11. The VCT-based method of claim 10, further comprising subtracting (220) the generated background of the composite part from the 3D volume of the composite part.

12. The VCT-based method of claim 1, wherein the detecting comprises calculating (222) global and local porosities of the 3D volume.

* * * * *